United States Patent
Kobayashi et al.

(10) Patent No.: US 9,101,556 B2
(45) Date of Patent: Aug. 11, 2015

(54) THERAPEUTIC AGENT AND THERAPEUTIC DEVICE FOR ALLEVIATING ISCHEMIA-REPERFUSION INJURY

(75) Inventors: Hirosuke Kobayashi, Sagamihara (JP); Toshihiro Shimbo, Sagamihara (JP); Kenichi Kokubo, Sagamihara (JP)

(73) Assignee: The Kitasato Institute, Tokyo (JP)

( * ) Notice: Subject to any disclaimer, the term of this patent is extended or adjusted under 35 U.S.C. 154(b) by 21 days.

(21) Appl. No.: 13/583,283

(22) PCT Filed: Mar. 2, 2011

(86) PCT No.: PCT/JP2011/054747
§ 371 (c)(1), (2), (4) Date: Nov. 27, 2012

(87) PCT Pub. No.: WO2011/111581
PCT Pub. Date: Sep. 15, 2011

(65) Prior Publication Data
US 2013/0108715 A1    May 2, 2013

(30) Foreign Application Priority Data
Mar. 10, 2010 (JP) ................ 2010-053405

(51) Int. Cl.
| | | |
|---|---|---|
| *A61K 33/00* | (2006.01) | |
| *A61K 9/00* | (2006.01) | |
| *A61M 16/00* | (2006.01) | |
| *A61M 16/12* | (2006.01) | |
| *A61M 16/20* | (2006.01) | |

(52) U.S. Cl.
CPC ............. *A61K 33/00* (2013.01); *A61K 9/0073* (2013.01); *A61M 16/0057* (2013.01); *A61M 16/12* (2013.01); *A61M 16/20* (2013.01)

(58) Field of Classification Search
None
See application file for complete search history.

(56) References Cited

U.S. PATENT DOCUMENTS

| | | | |
|---|---|---|---|
| 5,396,882 A * | 3/1995 | Zapol | 128/200.14 |
| 5,670,177 A | 9/1997 | Briend et al. | |
| 6,601,580 B1 | 8/2003 | Bloch et al. | |
| 6,656,452 B1 | 12/2003 | Zapol et al. | |
| 2005/0255178 A1* | 11/2005 | Bloch et al. | 424/718 |
| 2009/0035383 A1* | 2/2009 | Ohta et al. | 424/600 |

FOREIGN PATENT DOCUMENTS

| | | |
|---|---|---|
| CN | 101347451 A | 1/2009 |
| JP | 11513703 A | 11/1999 |

(Continued)

OTHER PUBLICATIONS

Prof. Shakhashiri "Gases of the Air", Chemical of the Week, vol. 103-1, 2007.*

(Continued)

*Primary Examiner* — Ernst V Arnold
*Assistant Examiner* — Kyung Sook Chang
(74) *Attorney, Agent, or Firm* — The Webb Law Firm

(57) ABSTRACT

Treatment for alleviating ischemia-reperfusion injury which has minimized risk of side effects and which can suppress neutrophilic infiltration and activation of platelets during ischemia reperfusion comprises administration by inhalation of a mixed gas comprising 21%-98% oxygen, 0.1%-4% hydrogen, 40-80 ppm nitrogen monoxide, and a remainder of inert gas such as nitrogen or helium to a patient undergoing reperfusion from immediately before the start of ischemia reperfusion until shortly after the start of reperfusion.

6 Claims, 2 Drawing Sheets

(56) References Cited

FOREIGN PATENT DOCUMENTS

| | | |
|---|---|---|
| JP | 2003532615 A | 11/2003 |
| JP | 2004509850 A | 4/2004 |
| WO | 2007021034 A1 | 2/2007 |

OTHER PUBLICATIONS

Fox-Robichaud et al. "Inhaled NO as a viable antiadhesive therapy for ischemia/reperfusion injury of distal microvascular beds", Journal of Clinical Investigation, vol. 101, No. 11, (Jun. 1998).*

Beckman et al., "Nitric oxide, superoxide, and peroxynitrite: the good, the bad, and the ugly", Invited Review, The American Physiological Society (1996).*

Strausz et al., "Reaction of Hydrogen Atoms with Nitric Oxide", Dept. of Chemistry, University of Alberta, Edmonton, Alberta, Canada (1963) pp. 347-358.*

Shinbo et al, "Breathing nitric oxide plus hydrogen gas reduces ischemia-reperfusion injury and nitrotyrosine production in murine heart", Am. J. Physiol Heart Circ Physiol 305, pp. H542-H550 (2013).*

Bloch, K. et al., Inhaled NO as a therapeutic agent, Cardiovascular Research, 2007, pp. 339-348, vol. 75.

Fukuda, K. et al., Inhalation of hydrogen gas suppresses hepatic injury caused by ischemia/reperfusion through reducing oxidative stress, Biochemical and Biophysical Research Communications, 2007, pp. 670-674, vol. 361.

Ohsawa, I. et al., Hydrogen acts as a therapeutic antioxidant by selectively reducing cytotoxic oxygen radicals, Nature Medicine, Jun. 2007, pp. 688-694, vol. 13, No. 6.

Shinbo, T. et al., Simultaneous inhalation of nitric oxide and hydrogen reduces infarct size in the mouse model of myocardial ischemia-reperfusion injury, Nitric Oxide, 2010, p. S28, vol. 22.

Hayashida et al., Inhalation of hydrogen gas reduces infarct size in the rat model of myocardial ischemia-reperfusion injury, Biochemical and Biophysical Research Communications, 2008, pp. 30-35, vol. 373.

Nanetti et al., Reactive oxygen species plasmatic levels in ischemic stroke, Mol Cell Biochem, 2007, pp. 19-25, vol. 303.

Huie et al., "The Reaction of NO with Superoxide", Free Rad. Res. Comms. 1993, pp. 195-199, vol. 18, No. 4.

Ohsawa et al., "Hydrogen acts as a therapeutic antioxidant by selectively reducing cytotoxic oxygen radicals", Nature Medicine 2007, pp. 688-694, vol. 13, No. 6.

Pacher et al., "Nitric Oxide and Peroxynitrite in Health and Disease", Physiol Rev. 2007, pp. 315-424, vol. 87, No. 1.

* cited by examiner

THERAPEUTIC AGENT AND THERAPEUTIC DEVICE FOR ALLEVIATING ISCHEMIA-REPERFUSION INJURY

TECHNICAL FIELD

This invention relates to a therapeutic agent, a therapeutic device, and a therapeutic method for alleviating injury to the affected parts, such as the cardiac tissue, and microangiopathy accompanying reperfusion which is experienced in reperfusion therapy for acute myocardial infarction (ischemia-reperfusion injury).

BACKGROUND ART

In infarction diseases such as myocardial infarction, cerebral infarction, and mesenteric thrombosis, ischemia reperfusion therapy which allows blood to reflow in tissue which was in an ischemic state by interruption of blood flow is often carried out by mechanically expanding the vessel in the infraction area or dissolving thrombi. In a transplanted organ after organ transplantation, blood flow is similarly restarted in tissue to which blood circulation ceased. It is known that when blood flow is restarted in a tissue, oxygen is suddenly delivered to the tissue which has been in an ischemic state, resulting in the occurrence of various physiological reactions including the generation of active oxygen (oxygen radicals) or other free radicals, neutrophilic infiltration, and activation of platelets, which cause worsening of organ derangement such as damage to the cardiac muscle (for example, myocardial infarction). Such phenomenon is referred to as ischemia-reperfusion injury or simply as reperfusion injury.

Nitrogen monoxide (NO) is a vasodilative substance derived from the endothelium. It is known that administration of nitrogen monoxide gas by inhalation has effects such as lowering the pulmonary arterial pressure by vasodilation in the lungs, increasing oxygenation of the entire body, suppressing activation of platelets, and suppressing activation and adhesion/coagulation of leukocytes. With respect to ischemia-reperfusion injury, inhalation of nitrogen monoxide gives a certain effect as demonstrated by the fact that it decreases the infarcted area and is effective at alleviating myocardial injury (see below-listed Patent Document 1 and Non-Patent Document 1).

However, while nitrogen monoxide has such protective activities, it has the problem that it reacts particularly with superoxide anions, which are produced intracellularly or extracellularly, resulting in the production of peroxynitrite which has an extremely high toxicity to the tissues. Accordingly, there is a high risk of side effects caused by the inhalation of nitrogen monoxide.

In recent years, it has been demonstrated that hydrogen ($H_2$), which is a reducing agent, selectively reacts with highly reactive species of active oxygen (such as hydroxyl radical <.OH> and peroxynitrite <ONOO$^-$>) and eliminates them. It is known that if hydrogen gas is administered by inhalation through the lungs, hydrogen is delivered to the entire body through the blood and can suppress lesions associated with oxygen radicals and eliminate free radicals which have a strong oxidizing power to cause cell injury. It has been reported that in ischemia reperfusion models of cerebral infarction and ischemia reperfusion models of the liver in mice, damage to organs and tissue at the time of ischemia reperfusion can be decreased by hydrogen (see below-listed Non-patent Documents 2 and 3). However, it is difficult to suppress neutrophilic infiltration and platelet activation which are observed at the time of ischemia reperfusion using only hydrogen inhalation.

PRIOR ART DOCUMENTS

Patent Document

Patent Document 1: JP 2004-509850 B

Non-Patent Documents

Non-patent Document 1: Cardiovascular Research, 75, 339-348, 2007
Non-patent Document 2: Nature Medicine 13, 688-694, 2007
Non-patent Document 3: Biochemical and Biophysical Research Communications, 361, 670-674, 2007

SUMMARY OF THE INVENTION

The object of the present invention is to establish a treatment technique for alleviating ischemia-reperfusion injury which has minimized risk of side effects and which can suppress neutrophilic infiltration and platelet activation at the time of ischemia reperfusion.

The present inventors attended to the fact that nitrogen monoxide and hydrogen have different action mechanisms, and they found that simultaneous inhalation of these two types of gases through the lungs can alleviate various events of ischemia-reperfusion injury and specifically the production of active oxygen and other free radicals as well as neutrophilic infiltration and platelet activation while preventing the side effects caused by nitrogen monoxide. As a result, they have completed the present invention.

The present invention is a gaseous inhalation pharmaceutical composition for alleviating ischemia-reperfusion injury consisting essentially of 21%-98% oxygen, 0.1%-4% hydrogen, 40-80 ppm nitrogen monoxide, and a remainder of an inert gas (such as nitrogen or helium).

This pharmaceutical composition, namely, a mixed gas containing oxygen, hydrogen, and nitrogen monoxide in an inert gas such as nitrogen or helium is administered by inhalation to a patient undergoing reperfusion from just before the start of ischemia reperfusion to shortly after the start of reperfusion. As a result, organ derangement due to reperfusion can be prevented.

From another standpoint, the present invention is a therapeutic device for alleviating ischemia-reperfusion injury by inhalation administration of the above-described pharmaceutical composition to a patient directly or via a ventilator, characterized by comprising respective gas sources for inert gas (such as nitrogen), oxygen gas, hydrogen gas, and nitrogen monoxide gas, a pressure regulator and a flow meter connected to each gas source, and a feed line for feeding each gas from its source, wherein all of the gas feed lines converge before administration to form a mixed gas consisting essentially of the inert gas, oxygen, hydrogen, and nitrogen monoxide.

From yet another standpoint, the present invention is a method of alleviating ischemia-reperfusion injury comprising administration by inhalation of a gaseous pharmaceutical composition consisting essentially of 21%-98% oxygen, 0.1%-4% hydrogen, 40-80 ppm nitrogen monoxide, and a remainder of an inert gas to a patient receiving ischemia reperfusion therapy from before the start of ischemia reperfusion until shortly after the start thereof.

According to the present invention, not only is the effect of alleviating ischemia-reperfusion injury which can be obtained greater than that obtained by the known method of inhalation of nitrogen monoxide gas only or inhalation of hydrogen gas only, but it is possible to prevent the problem of conventional treatment for alleviating ischemia-reperfusion injury by inhalation of nitrogen monoxide which has side effects in the form of tissue injury caused by the formation of peroxynitrite due to the reaction with superoxide anions. In addition, neutrophilic infiltration and platelet activation which could not be prevented with hydrogen inhalation can be suppressed.

By combined inhalation of nitrogen monoxide and hydrogen, the side effects of nitrogen monoxide inhalation can be prevented, and it is possible to achieve a synergistic effect of alleviating ischemia-reperfusion injury which is greater than the effect with either inhalation of nitrogen monoxide or inhalation of hydrogen, rather than a mere combined use effect. This is an extremely significant effect which could not be predicted by one skilled in the art. Alleviating ischemia-reperfusion injury improves the quality of life of patients undergoing reperfusion.

MODES FOR CARRYING OUT THE INVENTION

Figure 1:
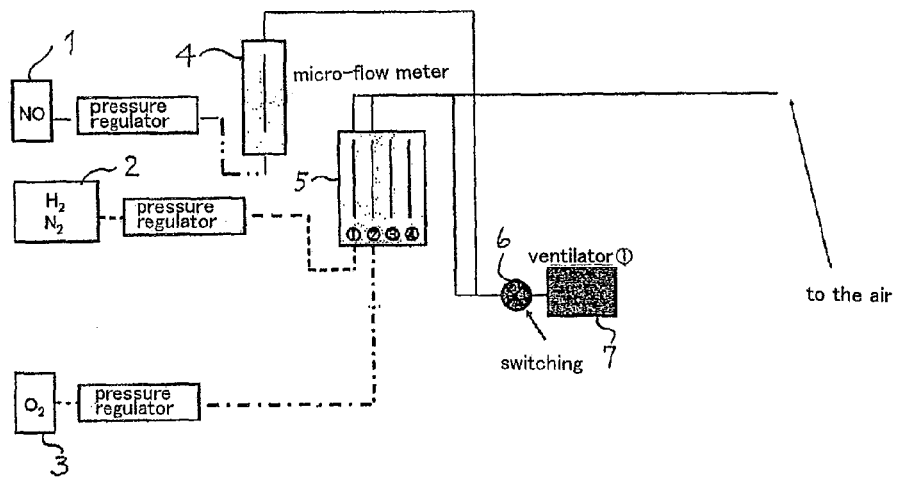
FIG. 1 is a schematic diagram showing the structure of an example of a therapeutic device which can be used to carry out combined inhalation of nitrogen monoxide and hydrogen according to the present invention.

The present invention can alleviate ischemia-reperfusion injury which is observed when carrying out ischemia reperfusion therapy, for example, on ischemic myocardial tissue in which blood flow has ceased in myocardial infarction patients by restarting blood flow by means of stent placement, endarterectomy, thrombolytic therapy, or the like. Such reperfusion of an infarcted area is also carried out in treatment for cerebral infarction or mesenteric thrombosis, and reperfusion injury can similarly occur during the treatment. Reperfusion injury can also occur after an organ transplant when restarting blood flow to tissue in transplanted organs to which blood flow ceased. The present invention can alleviate ischemia-reperfusion injury in any of such organs.

In the present invention, a gas which contains oxygen, hydrogen, and nitrogen monoxide in an inert gas such as nitrogen is administered by inhalation to a patient who is undergoing ischemia reperfusion in order to alleviate reperfusion injury from just before the start of reperfusion to shortly after the start of reperfusion. During surgery, for example, the period of administration can be from 5-60 minutes before ischemia reperfusion occurs until 30 minutes to 2 hours after reperfusion has occurred. A preferred administration period is from 10-30 minutes before the start of reperfusion until 10 minutes to 1 hour after the start of reperfusion.

The oxygen concentration in the gas which is administered by inhalation is in the range of 21%-98% and preferably is in the range of 21%-30%. If the oxygen concentration is too low, there is the risk of hypoxemia, while if it is too high, there is the risk of damage to the lungs. The hydrogen concentration in the gas is in the range of 0.1%-4% and preferably is around 2%. If the hydrogen concentration is too low, the effect of alleviating reperfusion injury decreases, while if it is too high, the danger of explosion develops. However, in air, hydrogen does not explode if its concentration is 4.7% or lower, even if a flame is brought close thereto. The concentration of nitrogen monoxide in the gas is in the range of 40-80 ppm, preferably 60-80 ppm, and most preferably approximately 80 ppm. If the nitrogen monoxide concentration is too low, the effect of alleviating reperfusion injury decreases, while if it is too high, it is difficult to prevent the above-described side effects of nitrogen monoxide even if hydrogen is present in the above-described concentration range. Nitrogen monoxide is already approved as a drug for ameliorating hypoxic respiratory failure accompanied by pulmonary hypertension in newborns (inhalation for up to 4 days at a concentration of 20 ppm), and a gaseous preparation having a nitrogen monoxide concentration of 800 ppm is commercially available. In the present invention, the remainder of the gas used as a pharmaceutical composition is an inert gas such as nitrogen gas or helium or other inert gas, but it may contain other gases, such as carbon dioxide, if present in minute amounts. Gases used as raw materials preferably have as high purity as possible.

In the present invention, "approximately" means that a variation of ±5% is permissible.

Inhalation therapy according to the present invention can be carried out using a device based on a conventional ventilator (artificial respirator) having an oxygen supply line connected through a pressure regulator and modified so as to have a nitrogen supply line, a hydrogen supply line, and a nitrogen monoxide supply line connected to the ventilator through their respective pressure regulators.

FIG. 1 shows the overall structure of one example of such a device. The illustrated device has a source 1 of nitrogen monoxide (NO), a source 2 of a mixed hydrogen/nitrogen gas prepared by diluting hydrogen ($H_2$) with nitrogen ($N_2$), and a source 3 of oxygen ($O_2$). Each of these gases is supplied from a gas cylinder. Hydrogen is supplied by diluting with nitrogen in order to avoid the danger of an explosion. The hydrogen concentration in the mixed hydrogen/nitrogen gas is preferably at most 5%, for example, and particularly preferably at most 4.7%. Similarly, although not shown in the drawing, out of safety considerations, the cylinder of nitrogen monoxide which is actually used is typically a cylinder containing a nitrogen-diluted nitrogen monoxide gas having a nitrogen monoxide concentration of around 1% (1000 ppm) or lower (such as the above-described gas having a nitrogen monoxide concentration of 800 ppm). The gas from each source passes through a pressure regulator and a micro-flow meter 4 or 5 and is mixed with each other to form a mixed gas, and the mixed gas is administered by inhalation to the lungs of a patient either directly or through a ventilator 7 after passing through a valve 6.

When nitrogen monoxide contacts oxygen, nitrogen monoxide may be consumed by a reaction forming nitrogen dioxide. Therefore, these two gases are preferably mixed immediately before reaching the valve. For this reason, in the illustrated device, a hydrogen/nitrogen mixed gas and oxygen gas pass through the same micro-flow meter 5, and they are mixed after their flow rate is adjusted. The resulting oxygen/hydrogen/nitrogen mixed gas is then mixed just before valve 6 with nitrogen monoxide gas which is supplied through a dedicated micro-flow meter 4. By switching the valve 6, the mixed gas is sent either directly to a patient or to a ventilator 7 and is administered by inhalation to the lungs of a patient.

It is also possible to use a mixed gas from a cylinder containing nitrogen monoxide (e.g., with a concentration of 800 ppm) and hydrogen (e.g., with a concentration of 20%) with a balance of nitrogen and dilute the mixed gas with oxygen and nitrogen (e.g., with a volume of 10 times).

EXAMPLES

Alleviation of ischemia-reperfusion injury by treatment according to the present invention was confirmed by the below-described animal experiments.

Experimental Method:

1. Mice Used for Experiment and Administration of Antibiotic 10-week old C57BL/6J male mice were used for the experiment. In order to eliminate the effect of hydrogen produced by bacteria present in the intestine, the animals were fed ad libitum water containing an antibiotic and usual feed for 4 days, and then they were fasted for 18 hours before the start of the experiment. However, during this period, the animals were allowed to take ad libitum the antibiotic-containing water. Before the start of the experiment, the hydrogen concentration in exhaled gas of each mouse was measured using a self-made circuit device for measuring the hydrogen concentration in expired gas in order to ascertain the effect of the antibiotic, and only mice for which the hydrogen concentration was below the measurable limit were used for the experiment. If the effect of hydrogen produced by enteric bacteria is not eliminated, there is a large variation in experimental results, and it is not possible to accurately evaluate the effect due to inhaled hydrogen.

2. Construction of Murine Myocardial Ischemia-Reperfusion Injury Models

After intraperitoneal administration of pentobarbital as an anesthetic and tracheal intubation, each animal was connected to an animal ventilator for respiration care. The left thorax was shaven and disinfected to carry out thoracotomy, and the left anterior descending coronary artery was ligated with a silk thread to maintain a state of ischemia for 60 minutes. The silk thread used for ligation was then released to cause reperfusion. Reperfusion was confirmed by the restart of blood flow. After confirming reperfusion, the thorax was closed, and ventilator care was continued until the animal awakened from anesthesia. After awakening from anesthesia, the tube was removed, and the animal received care in indoor air.

3. Time Zone of Inhalation and Concentration for Inhalation

The period of inhalation was the 35-minute period from 5 minutes before the to start of reperfusion (release of the ligature) until 30 minutes after the start of reperfusion. A group in which the animals did not inhale any gas of interest (just oxygen inhalation by an animal ventilator) was made a control group, and this group was compared with a group of hydrogen inhalation, a group of nitrogen monoxide inhalation, and a group of inhalation of the combination of hydrogen and nitrogen monoxide according to the present invention.

4. Preparation and Measurement of Cardiac Sections

After 24 hours had passed from the start of reperfusion, each animal was again subjected to anesthesia, thoracotomy, and ligation in the above-described manner. An Evans blue staining solution was injected through the left ventricle to identify the ischemic area. After confirming that the Evans blue solution had run through the coronary artery, the heart was excised. The excised heart was sliced in 1-mm widths to prepare heart sections. The prepared heart sections were stained with a TTC (2,3,5-triphenyltetrazolium chloride) staining solution to identify the infarcted area and were imaged using a stereoscopic microscope.

Based on the image which was obtained, each heart section was measured for the area of the LV (left ventricle), the AAR (area at risk=the ischemic area), and the area of Nec (necrosis; the infarcted area) using ImageJ image processing software to calculate the value of AAR/LV (proportion of the ischemic area in the left ventricle) and that of Nec/AAR (proportion of the infarcted area in the ischemic area). AAR/LV was used as an index for determining whether the same degree of ligation was achieved for all the sample animals, and Nec/AAR was used as an index of the effect of inhalation.

5. Circuit Structure and Gas Flow

The circuit structure was basically that shown in FIG. 1. Out of safety considerations, hydrogen was supplied from a nitrogen-diluted hydrogen gas cylinder containing 4% hydrogen in nitrogen. Nitrogen monoxide was supplied from a gas cylinder containing 800 ppm nitrogen monoxide in nitrogen. Using flow regulators and micro-flow meters, a mixed gas containing 30% oxygen, 2% hydrogen, and 80 ppm nitrogen monoxide in nitrogen was administered by inhalation to the lungs of to mice via an animal ventilator.

For comparison, a mixed gas having the same composition as described above except for not containing hydrogen or nitrogen monoxide was administered by inhalation to provide a nitrogen monoxide inhalation group (80 ppm nitrogen monoxide and 30% oxygen) and a hydrogen inhalation group (2% hydrogen and 30% is oxygen), respectively.

Figure 2:
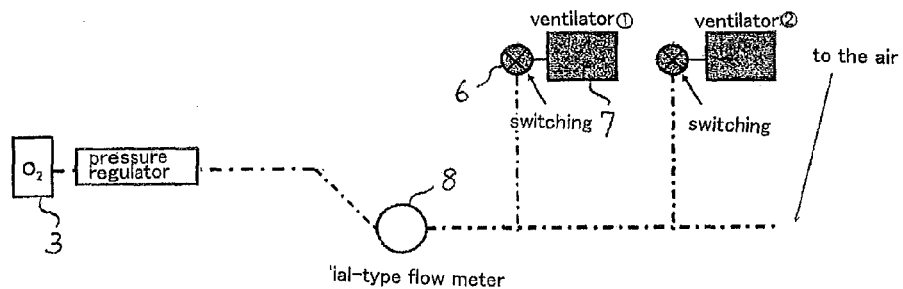
FIG. 2 is a schematic diagram showing the structure of a device used with ventilators for oxygen inhalation in an experiment.

When carrying out respiratory care by oxygen inhalation in the control group, as shown in FIG. 2, only oxygen from an oxygen source 3 was fed to an animal ventilator 7 through a dial-type flow meter 8.

Experimental Results

Figure 3:
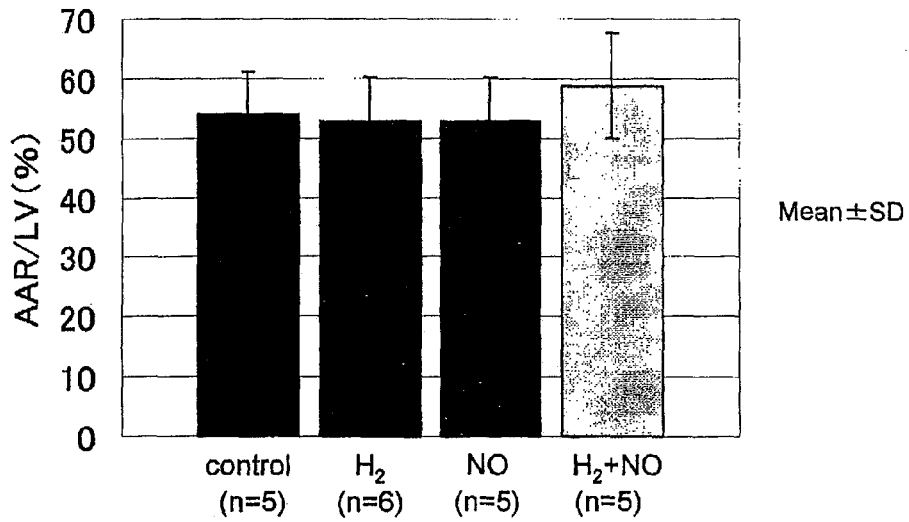
FIG. 3 is a graph showing the results of animal experiments (the proportion of ischemic area in the left ventricle).
Figure 4:
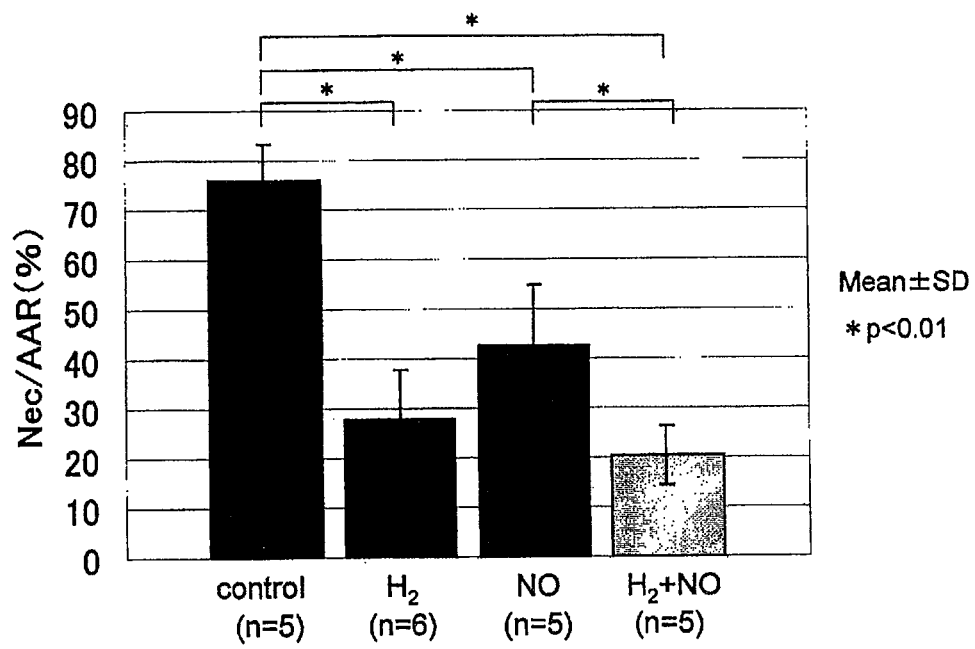
FIG. 4 is a graph showing the results of animal experiments (the proportion of infarcted area in the ischemic area).

The results of the experiments are shown in FIG. 3 and FIG. 4.

FIG. 3 shows the proportion (AAR/LV) of the ischemic area in the left ventricle for each group. The number of animals was as shown in the figure, and each value is shown as the mean±standard deviation. The proportion of the ischemic area varies depending upon the location of ligation of the left coronary artery. In order to evaluate the degree of reperfusion injury, the proportion of the ischemic area formed by ligation is desirably about the same for each group. From the figure, it can be seen that the value of AAR/LV was approximately the same for each group. Namely, approximately the same degree of ischemic area was prepared for each group.

FIG. 4 shows the proportion (Nec/AAR) of the infracted area in the ischemic area. The number of animals was as shown in the figure, and each value is shown as the mean±standard deviation. A group for which a significant difference was ascertained by a t-test is indicated by * ($p<0.01$).

Compared with the control group in which neither hydrogen or nitrogen monoxide was inhaled, the value of Nec/AAR was decreased for the hydrogen inhalation group, the nitrogen monoxide inhalation group, and the combined hydrogen/nitrogen monoxide inhalation group with a significant difference ascertained by a t-test. There was also a significant difference between the nitrogen monoxide inhalation group and the combined hydrogen/nitrogen monoxide inhalation group, showing that the group which had combined inhalation of hydrogen and nitrogen monoxide according to the present invention experienced a greater effect of alleviating reperfusion injury than the nitrogen monoxide inhalation group. There was no significant difference between the combined hydrogen/nitrogen monoxide inhalation group and the hydrogen inhalation group, but a tendency for the Nec/AAR value to further decrease in the infarcted area was observed in the combined hydrogen/nitrogen monoxide inhalation group.

As stated above, nitrogen monoxide has a side effect in which peroxynitrite having a strong cytotoxicity is produced. It is conjectured that hydrogen reduces the peroxynitrite and neutralize it, thereby decreasing injury due to the peroxynitrite. With just hydrogen inhalation, it is not possible to suppress neutrophilic infiltration or platelet activation which are observed at the time of ischemia reperfusion, but it is possible to suppress these phenomena by combined use of hydrogen and nitrogen monoxide.

In this experiment, hydrogen and nitrogen monoxide were allowed to inhale simultaneously, but it is possible to carry out just hydrogen inhalation or nitrogen monoxide inhalation either before, after, or both before and after the simultaneous inhalation. In this case, the hydrogen concentration and the nitrogen monoxide concentration in the gas for inhalation may be the same as the concentrations in the gas administered according to the present invention.

The invention claimed is:

1. A method of alleviating ischemia-reperfusion injury comprising administering by inhalation a gaseous pharmaceutical composition comprising 21% to 98% oxygen, 0.1% to 4% hydrogen, 40 ppm-80 ppm nitrogen monoxide, and an inert gas to a patient receiving ischemic-reperfusion therapy.

2. The method according to claim 1, wherein the gaseous pharmaceutical composition is administered to the patient before the start of ischemic-reperfusion therapy and continues thereafter.

3. The method according to claim 2, wherein the gaseous pharmaceutical composition is administered beginning about 5 minutes to about 60 minutes before ischemic-reperfusion therapy occurs until about 30 minutes to about 2 hours after ischemic-reperfusion therapy has occurred.

4. The method according to claim 3, wherein the gaseous pharmaceutical composition is administered beginning about 10 minutes to about 30 minutes before ischemic-reperfusion therapy occurs until about 10 minutes to about 1 hour after ischemic-reperfusion therapy has occurred.

5. The method according to claim 1, wherein the gaseous pharmaceutical composition comprises 21% to 30% oxygen, 2% hydrogen, 60-80 ppm of nitrogen monoxide, and an inert gas.

6. The method according to claim 1, wherein the gaseous pharmaceutical composition comprises 21% to 98% oxygen, 2% hydrogen, 60-80 ppm of nitrogen monoxide, and an inert gas.

* * * * *